(12) United States Patent
Akiba et al.

(10) Patent No.: US 6,251,068 B1
(45) Date of Patent: Jun. 26, 2001

(54) ENDOSCOPIC OBSERVATION SYSTEM

(75) Inventors: Haruo Akiba; Hitoshi Miyano; Itsuji Minami; Naotake Mitsumori, all of Omiya (JP)

(73) Assignee: Fuji Photo Optical Co., Ltd., Omiya (JP)

(*) Notice: Subject to any disclaimer, the term of this patent is extended or adjusted under 35 U.S.C. 154(b) by 0 days.

(21) Appl. No.: 09/313,770

(22) Filed: May 18, 1999

(30) Foreign Application Priority Data

May 18, 1998 (JP) ................................................ 10-135008

(51) Int. Cl.[7] ....................................................... A61B 1/07
(52) U.S. Cl. ............................ 600/182; 600/177; 600/180
(58) Field of Search ..................................... 600/177, 178, 600/180, 182; 385/116, 117; 348/68

(56) References Cited

U.S. PATENT DOCUMENTS

| | | | |
|---|---|---|---|
| 4,272,156 | * 6/1981 | Ishibashi et al. | 600/177 |
| 4,580,552 | * 4/1986 | Nishioka | 600/177 |
| 4,777,524 | * 10/1988 | Nakajima et al. | 600/167 |
| 4,929,070 | * 5/1990 | Yokota et al. | 600/177 |
| 5,305,736 | * 4/1994 | Ito | 600/109 |
| 5,730,702 | * 3/1998 | Tanaka et al. | 600/180 |

* cited by examiner

*Primary Examiner*—John P. Leubecker
(74) *Attorney, Agent, or Firm*—Oblon, Spivak, McClelland, Maier & Neustadt, P.C.

(57) ABSTRACT

An endoscopic observation means having least a couple of illumination means are provided at a distal end portion of an endoscopic insertion instrument, the illumination means being on the opposite sides of and substantially on the same plane as an optical image pickup means. Each one of the illumination means includes a light guide for transmitting on illumination light from a light source, and an illumination lens for dispersing illumination light over an imaging area of a subject under observation. Further, the endoscopic observation means includes an objective lens system having a variable observation distance. The illumination means on the opposite sides of the observation means are spaced apart from each other by such a distance as to hold illuminance in peripheral portions of an imaging area of the subject to a level not greater than 200%, preferably, in the range of 200% to 120% of an illuminance level in portions of the imaging area.

10 Claims, 15 Drawing Sheets

ENDOSCOPIC OBSERVATION SYSTEM

BACKGROUND OF THE INVENTION

1. Field of the Art

This invention relates generally to an endoscope for use in medical fields, and more particularly to an endoscopic observation system having an objective lens of a variable observation distance in its optical image pickup system.

2. Prior Art

Generally, the endoscopes, which are designed for introduction into a body cavity of a patient for medical examination or observation purposes, are largely constituted by a manipulating head assembly to be gripped and manipulated by an operator, and an elongated insertion instrument which is extended out from the head assembly for insertion into a body cavity. In order to permit observations within a dark body cavity, an intracavitary observation site of interest has to be illuminated with light which is supplied from outside. Therefore, an illumination means is usually provided alongside an endoscopic observation means or optical image pickup system at the distal end of the insertion instrument. The illumination means includes a light guide in the form of a bundle of fine fiber optics as a light transmission means, and an illumination lens is located in front of a light emitting end of the light guide. On the other hand, the optical image pickup system includes an objective lens to form an image of an intracavitary site under observation. Located at the focus of the objective lens is either an image pickup end of an image guide consisting of a bundle of fiber optics, or a solid-state image sensor device like CCD which functions to convert an optical image into electric signals. In the former case, that is, in the case of the so-called optical endoscope, images of an intracavitary site under observation are viewed through an eyepiece which is connected to the head assembly. In the latter case, that is, in the case of the so-called electronic endoscope, electric signals from the solid-state image sensor are sent to a video processor which generates video signals to display video images of the site under observation on a monitor screen.

In an endoscopic examination of an intracavitary site, for example, of a site within the stomach, it may become necessary to bring the endoscopic observation means to a position close to a particular gastric wall portion for closer examination after observing the site from a relatively distant position. At the time of an examination from an extremely close position, the focus of the objective lens of the endoscopic observation means needs to be adjusted correctly. In this regard, for example, Japanese Patent Publication 61-53698 discloses a focus adjusting mechanism for an endoscopic observation system. This focus adjusting mechanism makes it possible to adjust the focus of an objective lens to an intracavitary wall at an extremely small distance less than 1 cm, particularly at a distance of 1 mm to 2 mm. Observations from a position of such minimal observation distance can make it possible to examine intracavitary walls very accurately.

However, even if an objective lens is correctly focused on an intracavitary portion of particular interest, the endoscopic observation means cannot necessarily make accurate observation of the intracavitary portion. As mentioned hereinbefore, an intracavitary sites which is in darkness needs to be illuminated by the use of a light guide and an illumination lens, and the site under observation as a whole should be illuminated as uniformly as possible in terms of illuminance level. This is because existence of dark spots or dark shaded portions in part of the site under observation are hindrous to accurate endoscopic examinations. On the contrary, in case the illuminance level is extremely high in certain localities as compared with the remainder of an intracavitary site under observation, a high contrast between bright and shady portions in the entire areas of the site under observation can also make it difficult to examine the site precisely. Above all, in the case of an electronic endoscope using a solid-state image sensor device, overly illuminated bright portions can cause saturation to corresponding part of the image sensor pixels and result in images with blooming and smear. In addition, even if saturation of pixels does not take place, irregular variations in illuminance level will lower the dynamic range to make it difficult to produce images of good quality.

In this connection, for example, Japanese Laid-Open Patent Specification 6-169879 discloses an endoscopic illumination means which is arranged to suppress irregular variations in illuminance level across an observation area of an intracavitary site. According to this prior art, illumination means are located at equidistant positions on the opposite side of an observation means at the distal end of an endoscopic insertion instrument to project illumination light rays of substantially equal volumes from the two separate illuminating means. In this case, in order to concentrate the illumination light rays toward an intracavitary area under observation, the two illuminating means are located as close to the endoscopic observation means as possible within a range in which an optical image pickup portion of the observation means is free influences of harmful right rays.

The endoscopic insertion instrument to be introduced into a body cavity should be constructed as small as possible in diameter for easy and smooth passage through a path of insertion and for lessening pains on the part of the patient. Nevertheless, in addition to one endoscopic image pickup means and two illuminating means, the endoscopic insertion instrument is required to have a biopsy channel for insertion of a biopsy or surgical instrument or a passage for pumping a cleaning liquid to an observation window of the optical image pickup portion. Therefore, due to limitations in space, the two illumination means are inevitably required to have an extremely small aperture diameter and virtually take the shape of a point source of light. However, illumination light can be diffused by fitting an illumination lens in an illumination window face to face with a light emitting end of a light guide. By so doing, an intracavitary site under endoscopic observation can be irradiated with substantially uniformly in illuminance as long as the intracavitary site is located at a certain distance from the respective illumination means. However, the illumination lens are incapable of diffusing illumination light over a subject at an extremely short observation distance. Especially, in case the endoscopic observation means is located at a distance shorter than several millimeters, more specifically, at a very close distance of 1 mm to 2 mm, the illuminance distribution characteristics is such that the illuminance level is conspicuously hihg at a center position of the illumination window but abruptly drops toward peripheral portions thereof.

Therefore, the illumination system of the above-mentioned prior art, which has a couple of illumination means located on the opposite sides of an endoscopic observation window, is advantageous when concentrating illumination light on an examination site from a certain distance but has a drawback that the difference in illuminance level between center and peripheral areas of an imaging area of the site under examination becomes conspicuously large. Therefore, especially in the case of a solid-state image sensor, blooming and smear occurs to images on display, due to saturation of image sensor pixels in positions which correspond to high illuminance peripheral portions of an imaging area. Besides, due to degradations in dynamic range and S/N ratio, it becomes difficult to display on a monitor screen clear images which are necessary for accurate endoscopic examination or diagnosis.

SUMMARY OF THE INVENTION

With the foregoing situations in view, it is an object of the present invention to provide an endoscopic observation system which is simple in construction and yet capable of suppressing conspicuous variations in illuminance level across an imaging area of an intracavitary site under endoscopic examination from an extremely close minimal observation distance.

It is another object of the present invention to provide an endoscopic observation system which can suppress conspicuous differences in illuminance level between center and peripheral portions of an imaging area of an intracavitary site, which is under examination through a solid-state image sensor device, permitting to produce on a monitor screen clear images of the intracavitary site free of blooming and smear.

In accordance with the present invention, the above-stated objective are achieved by the provision of an endoscopic observation system which comprises: an optical image pickup system having an objective lens of a variable observation distance to pick up images of a subject from various distances through an observation window provided at a distal end of an insertion instrument of an endoscope; an illumination system having at least a couple of illumination means located on the opposite sides of and substantially in the same plane as the observation window of the optical image pickup system; the illumination means each having a light guide and an illumination lens for diverging illuminating light from the light guide toward a subject under examination; the illumination means on the opposite sides of the observation window being located in positions spaced from the observation window by such a distance as to hold illuminance in peripheral portions of an imaging area of the subject to a level lower than 200% of an illuminance level in a center portion of the imaging area at the time of observation from a minimal observation distance of the objective lens.

In this instance, differences in illuminance level between peripheral and center portions of an imaging area of an intracavitary site under observation should preferably be suppressed to a minimum. However, illumination light is normally in Gaussian distribution in volume having a peak at the center of an illumination lens. Therefore, if arrangements are made to use an angular range where variations in light volume are relatively small, the results would be a conspicuous drop in illuminance of a subject under observation and insufficient brightness in entire areas of images to be obtained. In this case, however, the difference in illuminance between peripheral and center portions of an imaging area of a subject under observation is about 20%. In case the optical image pickup system employs a solid-state image sensor device as observation means, end portions of an image area on display on a monitor screen correspond to the peripheral portions of an imaging area of a subject where the illuminance is held to a level which is not higher than 200% of an illuminance level in center portions of the imaging area. Namely, the peripheral portions of an imaging area correspond not to peripheral portions of a view field of an objective lens system but to end portions of an image area to be displayed on a monitor screen. For instance, in case a solid-state image sensor device or viewing screen has a masked area, the illuminance in end portions of an image area bordering on the masked area should not exceed 200% of an illuminance level in a center portion of the image area. In this connection, the longer the minimal observation distance, the more uniform becomes the illuminance distribution by an illumination lens. Accordingly, the present invention is particularly effective in observations from a minimal observation distance of an endoscope, more specifically, from a distance smaller than 1 cm because illumination lenses are located too close to a subject to produce dispersing or diverging effects on illumination light.

Minimization of differences in illuminance between center and peripheral portions of an imaging area of a subject under observation from a minimal distance normally results in a drop in illuminance level of the imaging area as a whole as compared with an illuminance level which is available in observations from ordinary distances. Generally, an illumination light source is equipped with a volume adjustor means like iris or stop to vary the volume of illumination light. Therefore, it is desirable to control illumination light in such a way as to increase its volume at the time of observation from a minimal observation distance. Alternatively, a third illumination means may be provided between the two illumination means mentioned above, arranging the third illumination means to function as an illuminance varying means. Particularly, in case a reversible electric motor is used as an objective drive means for focus adjustments, the third illumination means may be turned on and off by means of a switch which is actuated when the objective lens is moved to a minimal observation distance position by the reversible motor. Further, the endoscopic observation system may include a gain controller to increase the gain to a greater amount at the time of observation at a minimal observation distance position than in observations from ordinary observation distance positions. Furthermore, in case of an endoscope which has an annular hood fitted on a distal end portion of its insertion instrument in such a manner as to circumvent observation and illuminations means, a reflecting surface may be provided on the inner periphery of the hood for the purpose of illuminating a subject under observation additionally with reflected light and thereby moderating variations in illuminance across an imaging area of the subject. In such a case, it is desirable for the hood to be extended forward of the distal end of the endoscopic insertion instrument by a length equivalent with or greater than the minimal observation distance of the endoscope.

The above and other objects, features and advantages of the present invention will become apparent from the following particular description, taken in conjunction with the accompanying drawings which show by way of example preferred embodiments of the invention. Needless to say, it is to be understood that the present invention is not limited to the particular forms shown.

DESCRIPTION OF PREFERRED EMBODIMENTS

Figure 1:
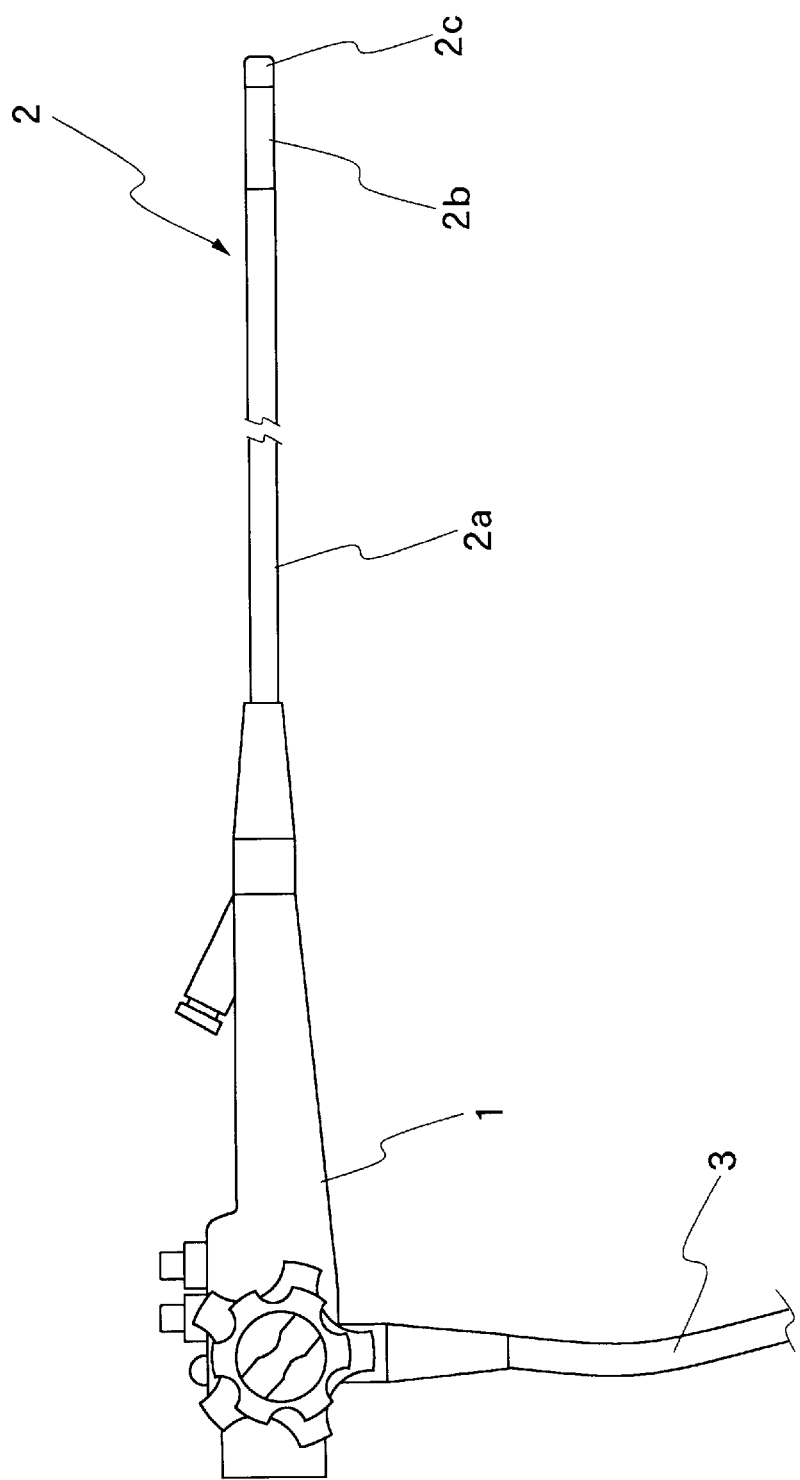
FIG. 1 is a schematic illustration of an endoscope, showing its general layout.

Hereafter, the present invention is described more particularly by way of its preferred embodiments with reference to the accompanying drawings. Firstly, shown in FIG. 1 is the general layout of an endoscope, in which indicated at 1 is a manipulating head assembly of the endoscope, at 2 an insertion instrument to be introduced into a body cavity or the like, and at 3 a universal cable. The endoscopic insertion instrument 2 is extended out from the manipulating head assembly 1 which is gripped and manipulated by an operator. A major part of the endoscopic insertion instrument 2 is constituted by a flexible section 2a which is flexibly bendable in arbitrary directions along a path of insertion. Connected successively to the fore end of the flexible section 2a are an angle section 2b and a rigid tip end section 2c. The angle section 2b can be manipulated into a bent form to turn the rigid tip end section 2c into a desired direction. Incorporated into the rigid tip end section 2c is an image pickup system which is necessary for endoscopic observation of an intracavitary site.

Figure 2:
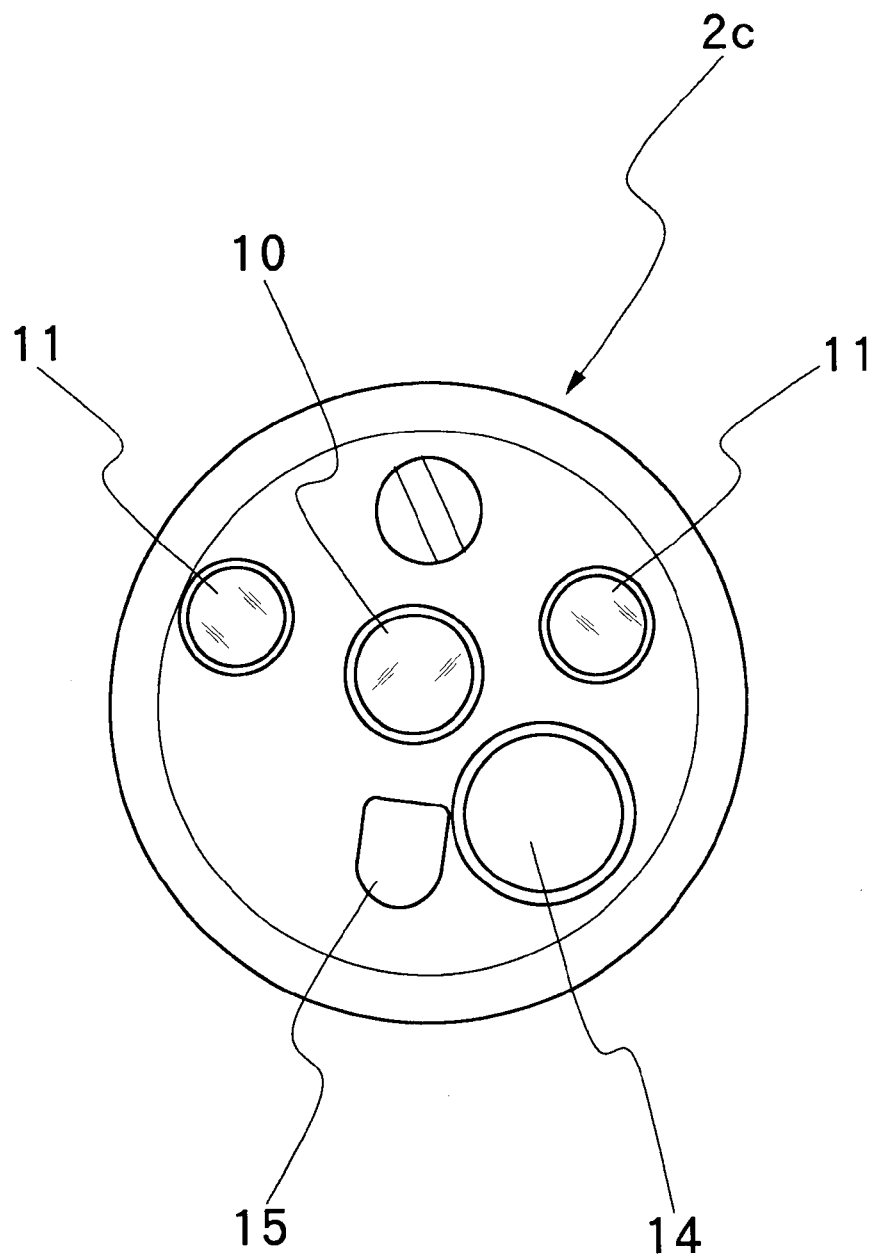
FIG. 2 is a schematic end view of a fore distal end portion of an endoscopic insertion instrument.
Figure 3:
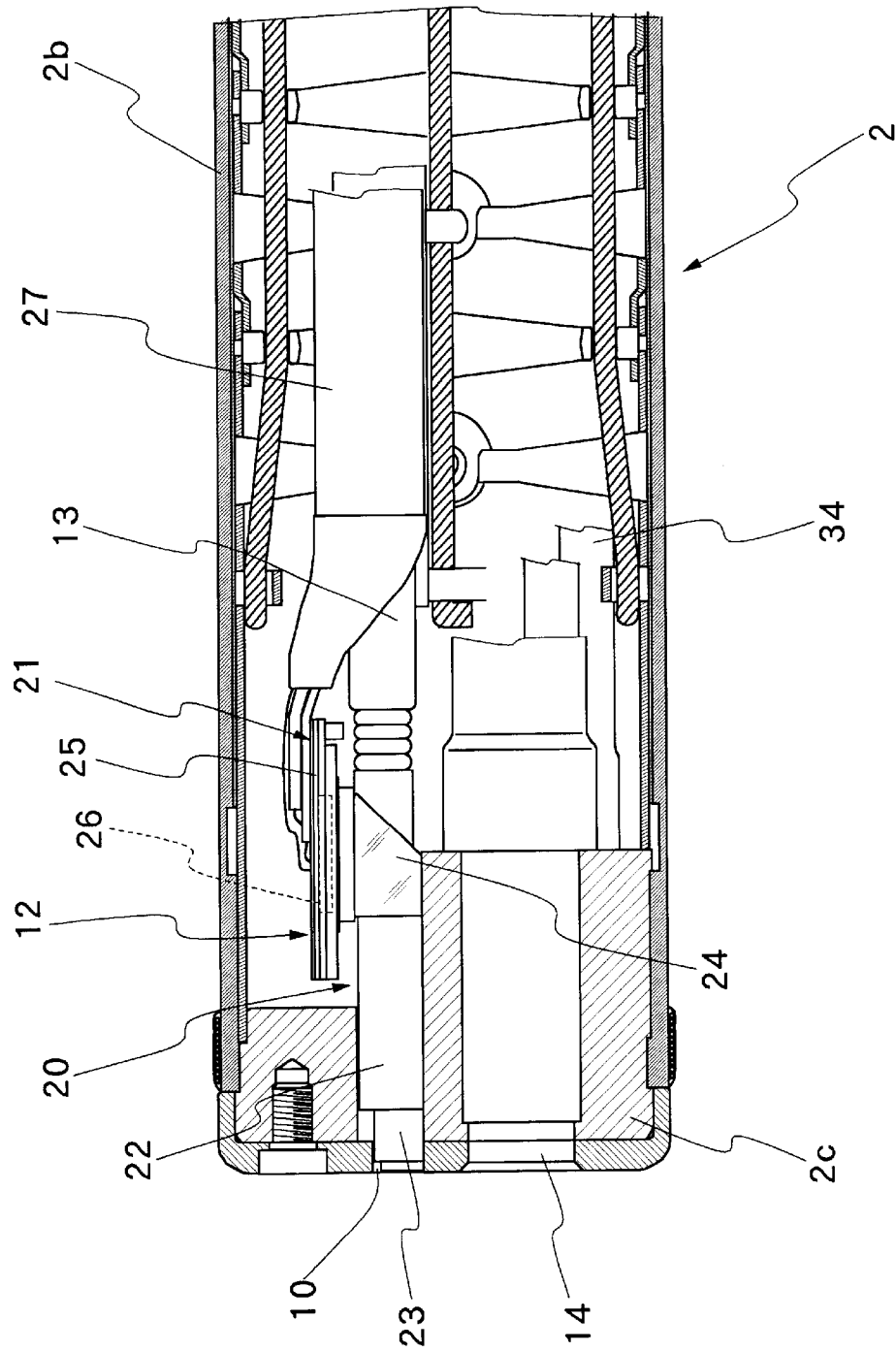
FIG. 3 is a schematic sectional view of the fore distal end portion of the endoscopic insertion instrument.
Figure 4:
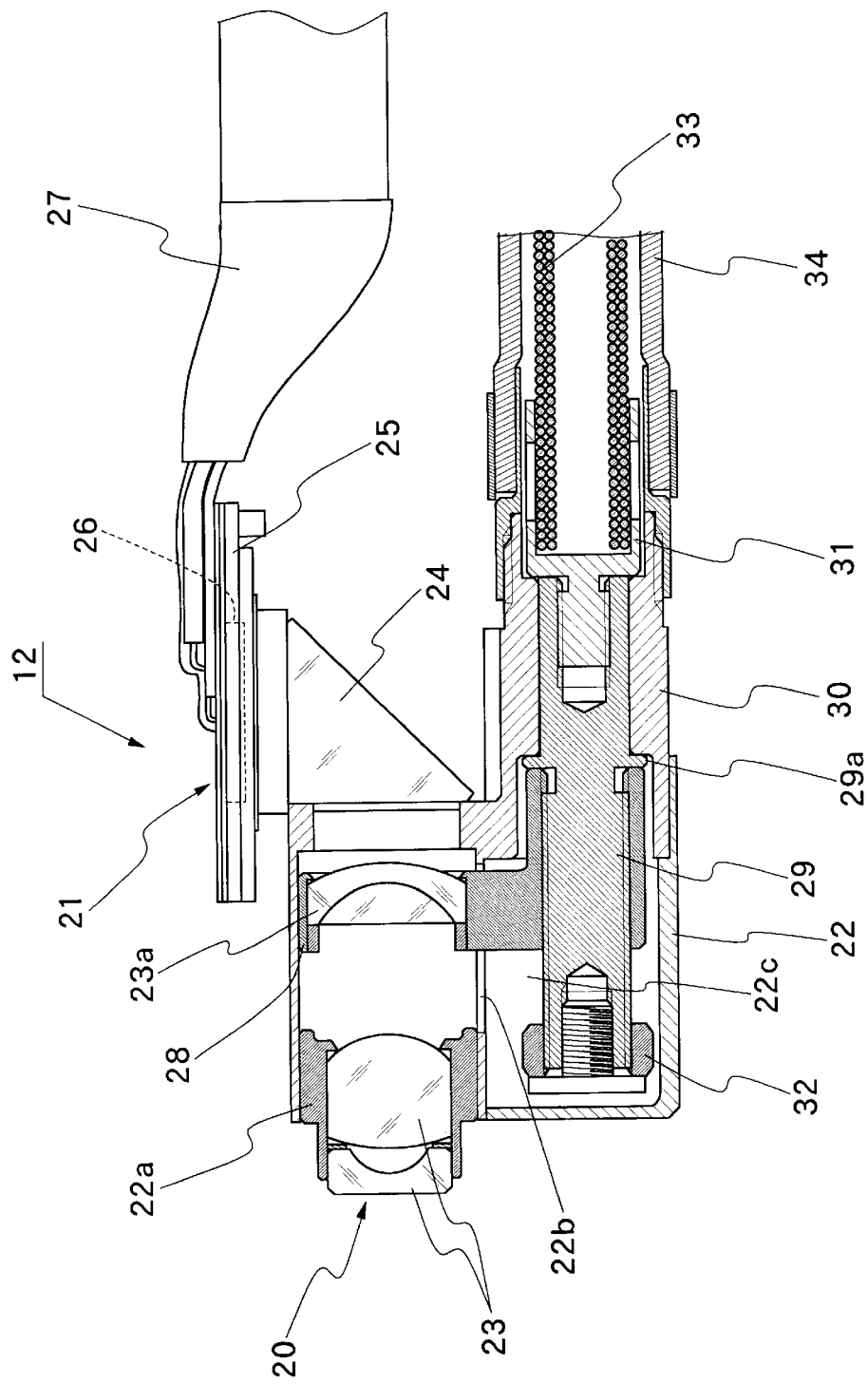
FIG. 4 is a schematic sectional view taken through an optical image pickup system or observation system.
Figure 5:
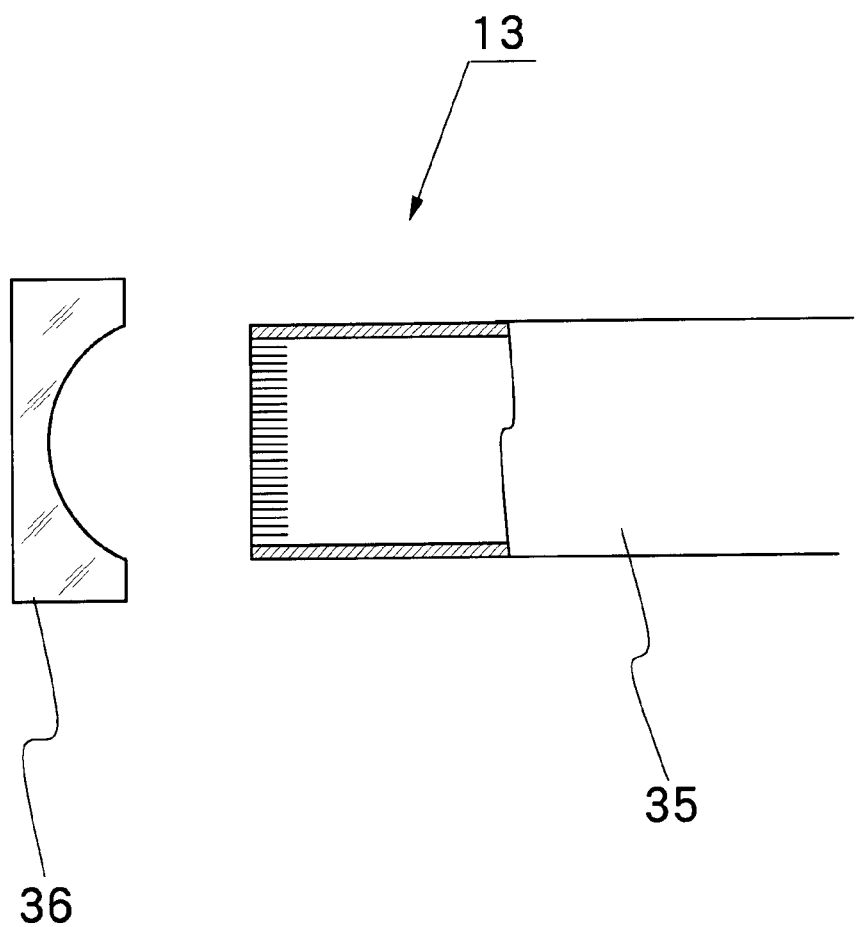
FIG. 5 is a partly cutaway schematic view of an illumination means.

As shown in FIG. 2, illumination windows 11 are provided on the opposite sides of an observation window 10 on a distal end face of the rigid tip end section 2c. The observation window 10 and illumination windows 11 are located on the same plane, and the two observation windows 11 are located substantially in equidistant positions from the observation window 10. As seen in FIGS. 3 and 4, an optical image pickup system of the observation means is fitted in the observation window 10. On the other hand, 22 an illumination means 13 is fitted in each one of the illumination window 11 as shown in FIG. 5. Further, in addition to the observation and illumination windows 10 and 11, an outlet opening 14 of a biopsy channel is opened in the distal end face of the rigid tip end section 2c to extend forceps or other biopsy or surgical instrument into a body cavity, along with a nozzle 15 which serves to supply a cleaning fluid toward the observation window 10. The construction of the rigid tip end section 2c which is shown in the drawings is of a forward view type which has a view filed in a straightforward axial direction of the endoscopic insertion instrument 2. In the case of a side view type endo scope, the above-described components of the endoscopic observation system are located in a flat surface on a lateral side of the rigid tip end section 2c.

An optical image pickup means 12 which is fitted in the observation window 10 includes, for example, an optical objective lens system 20 and an image pickup unit 21 as shown in FIG. 4. The objective lens system 20 includes a group of objective lenses 23 which are mounted in a lens tube 22a 16 of a lens block 22, and a prism 24 which is fixed in position behind the objective lenses 23 of the lens block 22 by the use of an adhesive means or the like to turn the optical axis of the lens system through 90 degrees. The image pickup unit 21 includes a solid-state image sensor device 26 like CCD which is mounted on a wiring board 25. The solid-state image sensor device 26 is fixedly cemented to the prism 24 in a plane which is located at the focus of the objective lens system 20. A large number of wires which are connected to the wiring board 25 are bundled into a single cable 27. This cable 27 is passed through the endoscopic insertion instrument 2 and extended into the universal cable 3 via the manipulating head assembly 1. The universal cable 3 is provided with a connector (not shown) at its proximal end to be disconnectibly connected to a processor.

Of the lenses which constitute the objective lens system 23, a rear lens group which consists of one or a plural number of lenses, as indicated at 23a, is movable in the direction of optical axis. When the observation window 10 is relocated closer to an intracavitary examination site, the focus is adjusted exactly on the examination site by shifting position of the movable lens 23a in the direction of optical axis. The movable lens 23a is supported on a movable lens frame 28 independently of the lens 22a tube of the front lens group. The lens frame 28 is moved in the direction of optical axis along a guide portion 22b which is provided on the main block 22. Further, the lens frame 28 is extended into a drive chamber 22c through the guide portion 22b of the main block 22 and, for example, held in threaded engagement with a helicoid screw shaft 29 within the drive chamber 22c. The screw shaft 29 is rotatably supported on a support member 30 which is connected to the main block 22. A stopper 29a provided on the screw shaft 29. In addition, a connector member 31 is provided at a rear end of the screw shaft 29. Accordingly, the supported member 30 is gripped between the stopper 29a and connector member 31 thereby to block movements of the screw shaft 29 in any direction except for movements in the rotational direction. Further, a nut 32 is provided at a fore end of the screw shaft 29 to serves as a stopper, so that the lens frame 29 is permitted to reciprocate between the nut 32 and the stopper 29a.

Figure 6:
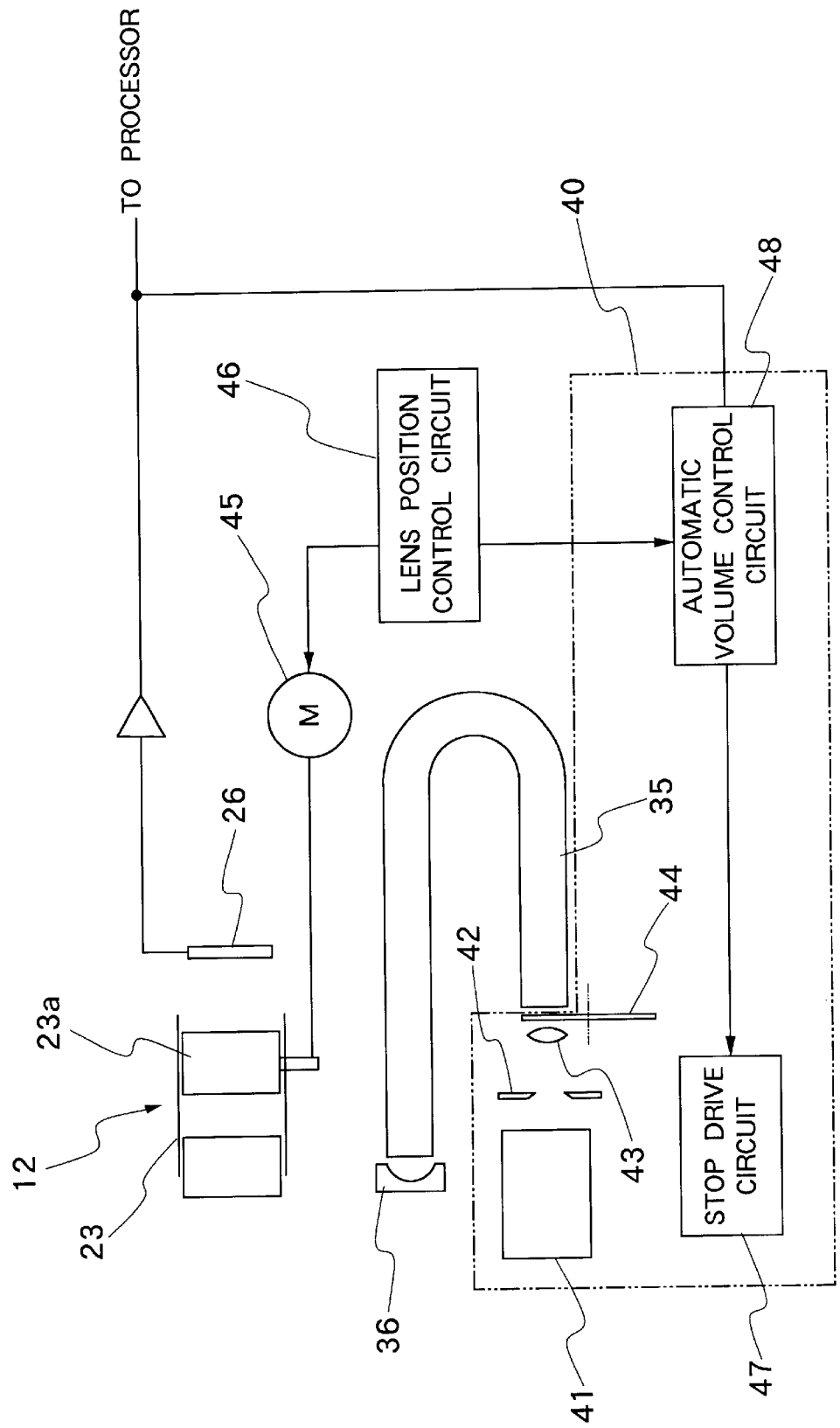
FIG. 6 is a diagram which illustrates arrangements of illumination and observation systems.

Coupled with the connector member at the rear end of the screw shaft 29 is a flexible rotation transmission shaft 33 which is constituted, for example, by a double coil tubes of tightly wound coils for rotations in both right and left directions. Further, the flexible shaft 33 is passed through a flexible tube 34 which is connected to the support member 30. Thus, the flexible shaft 33 and the flexible tube 34 constitute a control cable. The control cable is extended into the manipulating head assembly 1, where the proximal end of the flexible tube 34 is retained in a fixed state. On the other hand, the proximal end of the flexible shaft 33 is coupled with a reversible rotational drive means, for example, to a reversible motor 45 (FIG. 6). Accordingly, upon actuating the motor, the flexible shaft 33 is rotated about its axis within the flexible tube 34, and the screw shaft 29 is also put in rotation to displace the lens frame 28 of the movable lens 23a over a predetermined distance in the direction of the optical axis. If desired, arrangements may be made to turn the flexible shaft 33 by a manual operation.

On the other hand, as shown in FIG. 5, the illumination means 13 which is fitted in each illumination window 11 is constituted by a light guide 35 and an illumination lens 36. The illumination lens 36 is disposed within the illumination window 11, and a light emitting end of the light guide 35 is located face to face with the illumination lens 36. The light guide 35 consists of a bundle of fiber optics, which is flexible and bendable in arbitrary directions. This light guide 35 is extended through the endoscopic insertion instrument 2 and into the universal cable 3 via the manipulating head assembly 1, and disconnectibly connected to a light source 40 through a light connector (not shown). As shown in FIG. 6, the light source 40 includes a source lamp 41 which is located face to face with a light input end of the light guide 35. Located between the light input end of the light guide 35 and the source lamp 41 are, from the side of the source lamp 31, a stop 42, a condenser lens 43 and a rotary color filter 44.

Two illumination windows 11 are provided on opposite sides of the observation window 10. In this instance, illumination light from each illumination window 11 is diverged through the illumination lens 36 with a predetermined angle of divergence. The objective lens group 23 of the objective system 20 which is fitted in the observation window 10 includes the movable lens 23a which is movable in the direction of optical axis, so that it can take images of an object at a close distance of a few millimeters or less, for example, at a distance of 1 to 2 millimeters. As seen particularly in FIG. 6, the proximal end of the flexible shaft 33 is connected to the motor 45. This motor 45 is provided within a housing of the manipulating head assembly 1 which is in turn provided with a lens position controller 46 for the control of the objective lens position. The lens position controller 46 includes a motor operating member like a push-button, for example, which can be manipulated with a finger of an operator's hand which grips the manipulating head assembly 1. Upon manipulating the motor operating member, the motor 45 is put in a forward or reverse rotation to shift the movable lens 23a between a normal distance observation position and a minimal close distance observation position. In addition to these observation positions at the stroke ends, the movable lens 23a can be located at any intermediate observation position within its stroke length.

Figure 7:
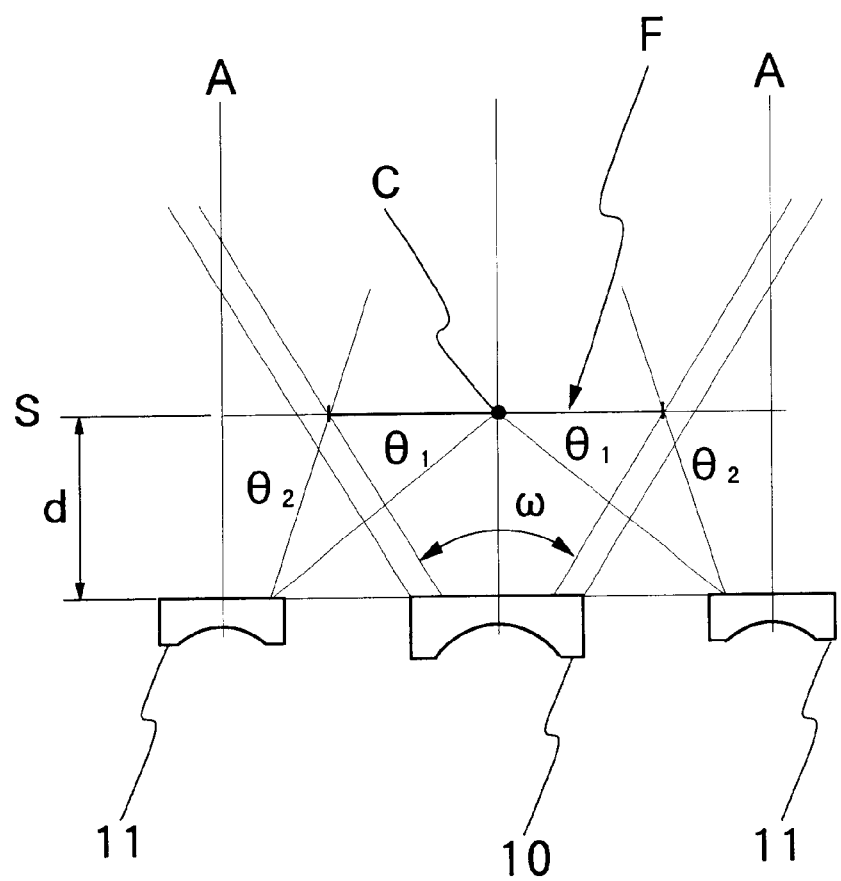
FIG. 7 is a diagrammatic illustration explanatory of relations between a view field of an observation window and ranges of illumination light which is projected through illumination windows at the time of an endoscopic observation from a minimal observation distance.

The diagram of FIG. 7 shows the relations between the observation view field of the objective lens system 20 in the observation window 10 and the illumination range of the illumination lens 36 in each illumination window 11 in an endoscopic observation at a minimal close distance. In this figure, the letter d stands for a minimal observation distance, and "ω" a view field of the optical objective lens system 20 for a subject S which is at the minimal observation distance "d". In this particular case in which the optical image pickup system 12 is provided with the solid-state image sensor 26, the images which are picked up through the solid-state image sensor 26 are displayed on a monitor screen having an actually imaging or observing area F. The letter "C" indicates the center of the imaging area F. The imaging area F is an actual endoscopic image observation range, which is different from the view field of the objective system 20 itself. Namely, the picture images which are displayed on a monitor screen is limited to certain areas around the center of the view field of the optical objective lens system 20. In displaying endoscopic observation images on a monitor screen, in some cases the imaging area is further narrowed down by masking peripheral areas of the screen. Therefore, the imaging area F represents an actual image area on the monitor screen or an unmasked image area in case peripheral portions of images are masked in the course of image processing operations or in case an image pickup area is limited by putting a masking member on part of the solid-state image sensor device 26.

Illumination light is projected in a dispersing fashion toward the subject of examination S from the illumination windows 11 which are located in equidistant positions on the opposite sides of the observation window 10. Of the illumination light rays from each illumination window 11, the center C of the imaging area F is illuminated with the light rays which come at an angle of θ1 relative to the optical axis A, while end portions of the imaging area F are illuminated with light rays which come at an angle of θ2. Accordingly, when the subject of examination S is irradiated with light rays from the respective illumination windows 11, the illuminance or illumination light intensity is strongest at the at the position of the optical axis A and drops continuously toward peripheral portions. The variations in illuminating light distribution become more conspicuous and abrupt when the illumination lenses 36 are located closer to the subject of examination S. As shown particularly in FIG. 8, when the illumination windows are located at the minimal observation distance d of a few millimeters, extremely abrupt variations in illuminance distribution take place at or in the vicinity of the optical axis A. Since the illumination windows 11 are provided at two spaced positions corresponding to the opposite ends of the imaging area F, the subject of examination S is irradiated with light rays from both of the two illumination windows 11 at and in the vicinity of its center portions. As a result, the subject of examination S in the imaging area F is irradiated with illumination light which has an illuminance distribution as indicated by two-dot chain line in FIG. 8.

Figure 8:
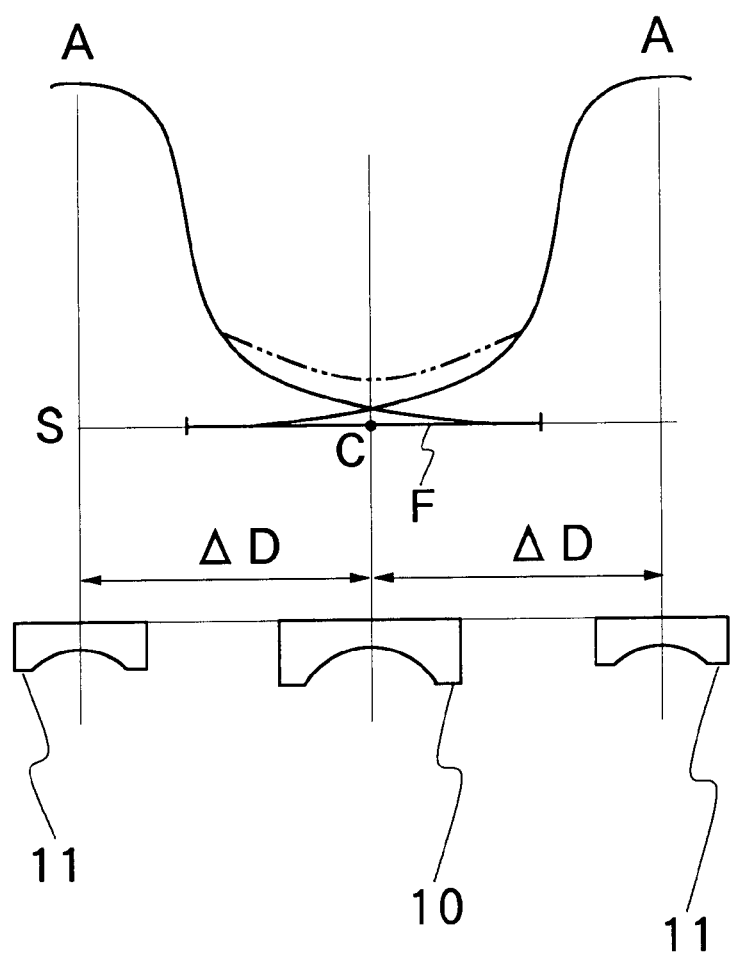
FIG. 8 is a diagram of illuminance distribution by the illumination means at a minimal observation distance position.

As clear from FIG. 8, when an imaging area F is of a given breadth is irradiated with light from illumination windows 11 which are located at the distance of Δd from the optical axis A which passes through the center of the imaging area F, variations in illuminance across the imaging area becomes smaller and lower as the distance Δd is increased. Namely, when the two illumination windows 11 are located at a greater distance from the observation window 10, variations in illuminance in the imaging area F become smaller but the illuminance becomes lower as a whole. On the contrary, in case the distance Δd is reduced, namely, in case the two illumination windows 11 are located closer to the observation window 10, the illuminance in the imaging area F as a whole including the center C becomes higher but differences in illuminance between center and peripheral portions of the imaging area F becomes greater under the direct influence of that part of the illuminance distribution characteristics of the illumination windows 11 where the illumination light volume varies abruptly.

In this connection, particularly in case the solid-state image sensor device 26 is employed as endoscopic image pickup means, the differences in illuminance or illumination light intensity between center and peripheral portions of the imaging area F should be suppressed to a minimum in order to obtain clear images. As long as illuminance in brightest portions of a subject S, that is, illuminance in brightest peripheral portions of the imaging area F is suppressed to a level which is less than two times an illuminance level in darkest portions of the subject, that is, an illuminance level at the center C of the imaging area F, the dynamic range of the solid-state image sensor device 26 can be adjusted in such a way as to obtain images of favorable S/N ratio. If the illuminance level in brightest portions becomes more than two times as high as that of darkest portions, the quality of images to be displayed on the monitor screen will be degraded beyond a range of sensitivity adjustment by an image processor.

Thus, the smaller the differences in illuminance across the imaging area F, the higher becomes the quality of images. Therefore, in order to use moderately varying portions of the illuminance distribution, the illumination windows 11 should be located in farther positions away from the observation window 10. However, location of the illumination windows 11 in remote positions will lead to a drop in illuminance level of the imaging area F as a whole and therefore will result in darker images. For this reason, preferably the difference in illuminance level between center and peripheral portions of the imaging area F should not be suppressed to an extremely small value. The illuminance level of the imaging area F as a whole may become insufficient in some cases if the illuminance difference is made smaller than 20%. More particularly, it is desirable to hold an illuminance level in the brightest portions within a range of 2 to 1.2 times, preferably 2 to 1.5 times an illuminance level in the darkest portions within the imaging area F. Most preferably, the illuminance level in the darkest portions should be approximately 1.8 times an illuminance level in the darkest portions in the imaging area F.

On the basis of predetermined factors such as the range of the display image area and the angle of divergence of the illumination lens 36, the distance $\Delta d$ of the illumination windows 11 from the observation window 10 is adjusted in such a way as to have the illuminance distribution at the minimal observation distance d within the above-described range. Namely, the distance $\Delta d$ is adjusted such that the illuminance of light rays which fall on the center of the imaging area F at the angle of $\theta 1$ at a minimal observation distance is 2 to 1.2 times, more preferably, 1.8 times as high as the illuminance of light rays falling on end portions of the imaging area F at the angle of $\theta 2$. By so adjusting, it becomes possible to obtain clear images while suppressing losses of source light to a minimum. Besides, although the difference in illuminance level is controlled to the above-mentioned range on the basis of a minimal observation distance, it is further narrowed down at farther observation positions because illumination light rays from the respective illumination windows 11 are dispersed to a greater degree correspondingly to a shift of observation position remote from the minimal observation position, and a subject of examination is irradiated with illumination light of more uniform distribution, permitting to obtain clear images.

Thus, in order to minimize the difference in illuminance between central and end portions of the imaging area F at a minimal observation distance, it is necessary to use a low illuminance part of illumination light rays from the illumination means 13, away from the optical axis A at the center of the illuminance distribution. Therefore, the illuminance of the imaging area F can become too low if the illumination light volume from the source lamp 41 is of an ordinary level which is used for observations from normal distances. In such a case, it is desirable to increase the volume of source light upon detecting a shift of the movable lens 23a to the minimal observation distance d through a sensor or the like.

As clear from FIG. 6, the light source is capable of varying the volume of illumination light to be transmitted from the source lamp 31 to the light guide 35. To this end, the aperture area of the stop 42 is varied by a stop drive circuit 47. In this regard, Y signals of video signals which are obtained from the solid-state image sensor device 26 are fed to an automatic light volume control circuit 48, which controls the volume of illumination light to be transmitted to the light guide 35 according to the levels of Y signals fed back thereto. Therefore, the automatic light volume control circuit 48 is utilized in such a way as to increase the aperture area of the stop 42, that is, to increase the light volume of illumination light to the light guide 35 when the movable lens 23a is shifted to the minimal observation distance position d. For this purpose, operating signals of a lens position controller 46 are fed 11 to the automatic light volume control circuit 48, and, as soon as the movable lens 23a is shifted to the minimal observation distance position d, the aperture area of the stop 42 is increased to ensure that a clear image of the imaging area F as a whole is picked up by the solid-state image sensor device 26.

In this regard, instead of adjusting the light volume, the gain of the image sensor may be adjusted by means of a gain controller which is connected to the solid-state image sensor device 26. In some cases, clear images can be obtained without automatically controlling a source light volume or a gain controller in relation with operation of the lens position controller 46 as described above. In such a case, there may be provided a manual switch for manually varying a source light volume or gain of the image sensor whenever necessary.

Figure 9:
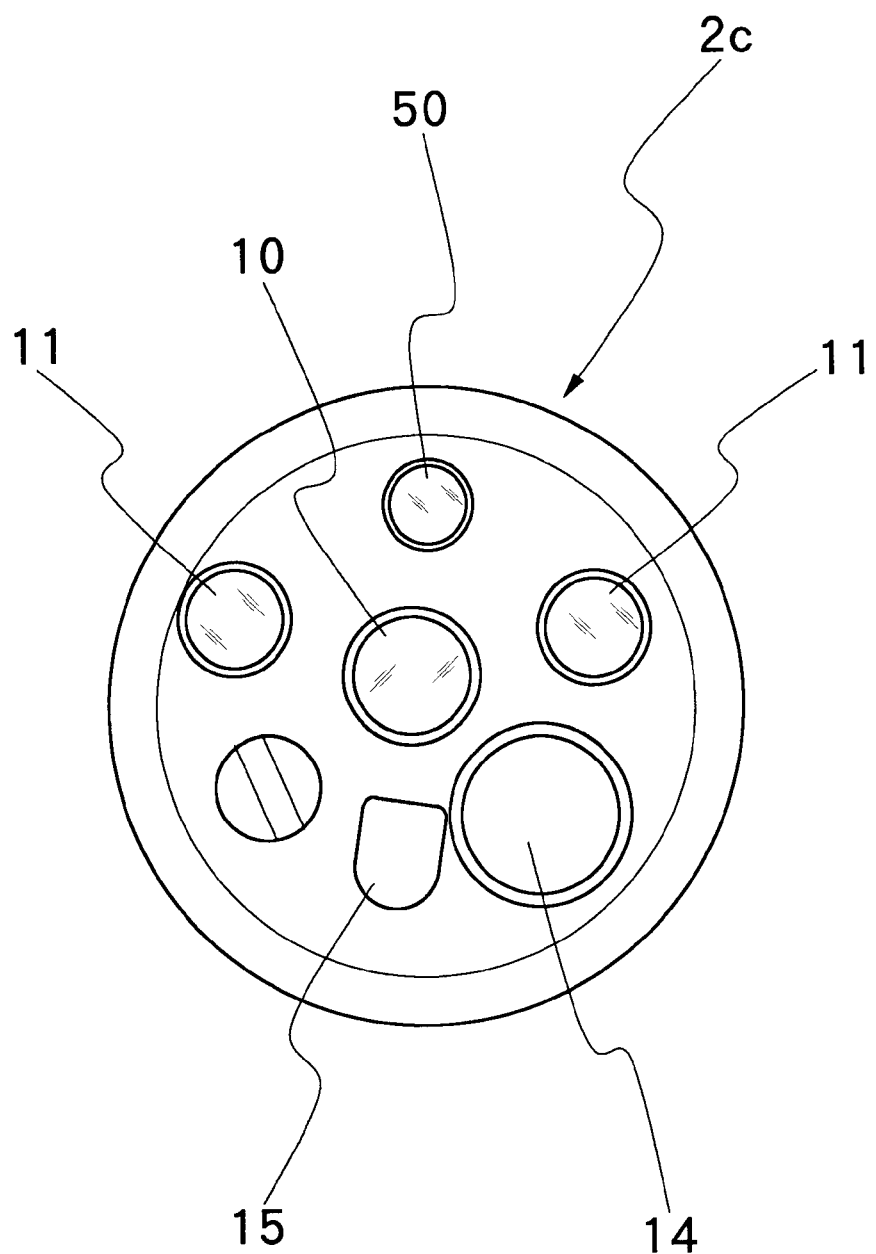
FIG. 9 is an outer view of a fore distal end portion of an endoscopic insertion instrument incorporating a third illumination means.

Alternatively, as shown in FIG. 9, there may be provided a third illumination means 50 between the two illumination windows 11. In this case, the third illumination means 50 functions to project supplemental or auxiliary light rays between the two main illumination windows 11. As for the third illumination means 50, part of the light guide 35 is branched off and its light emitting end is disposed face to face with a third illumination lens having an optical axis directed toward the center C of the imaging area F. The provision of the third illumination means 50 serves not only to enhance the illuminance level of the imaging area F as a whole but also to suppress variations in illuminance across the imaging area F. The third illumination means 50 may be arranged to be lit on all the time during an examination, but it is preferred to be lit on only when additional illumination is required. More specifically, it is preferred to lit on the third illumination means automatically when the movable lens 23a is shifted to the minimal observation distance position d. As the third illumination means, a white LED or other light emitting device may be employed in place of the above-described light guide.

Figure 10:
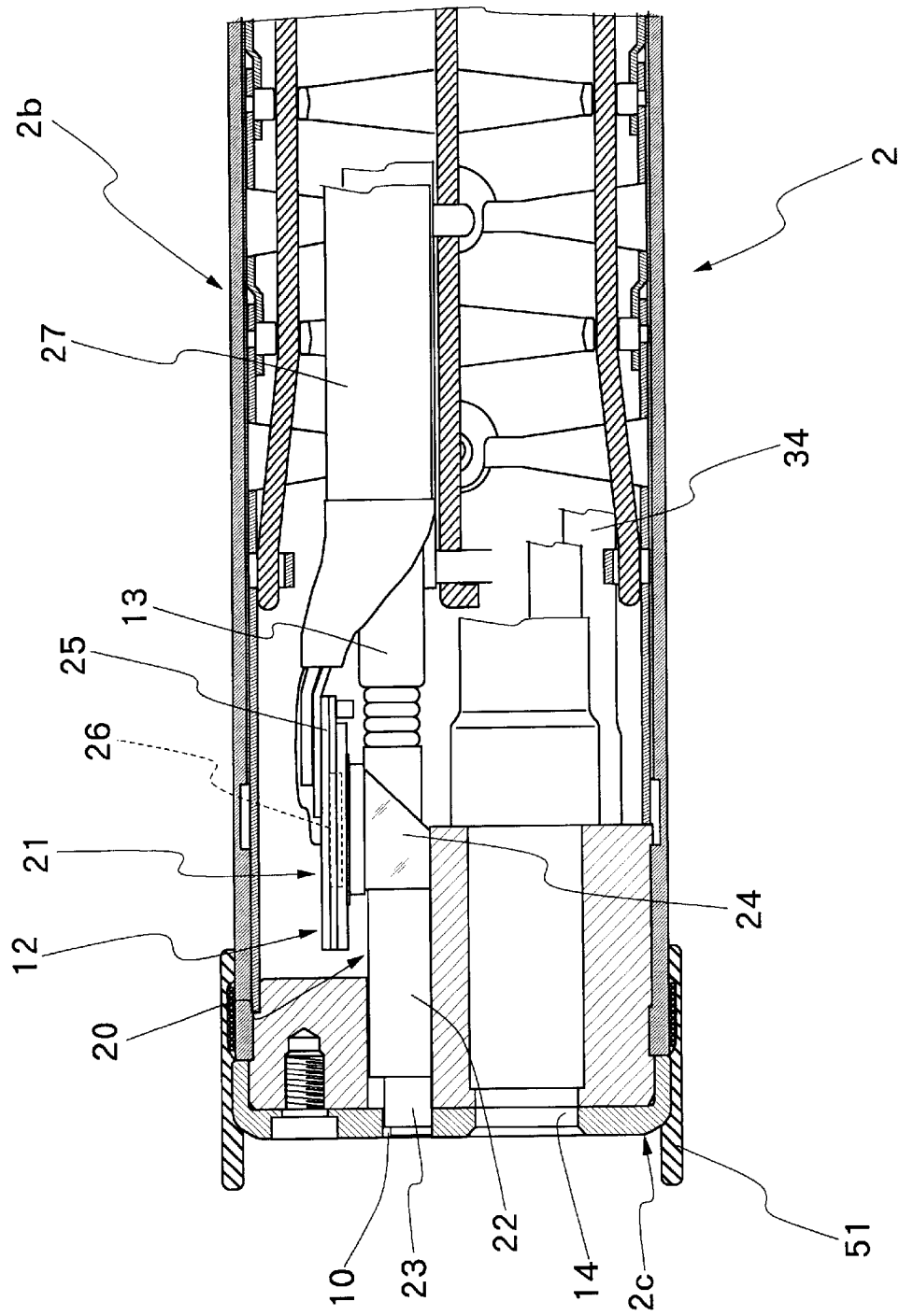
FIG. 10 is a sectional view similar to FIG. 2 but showing a hood which is fitted on the endoscopic insertion instrument.

Further, as shown in FIG. 10, for the purpose of moderating variations in illuminance distribution, a hood 51 may be put on the tip end section 2c of the insertion instrument 2 in such a way as to circumvent a subject of examination S which is under direct illumination from the illumination windows 11. At the time of an examination from a position at or around the minimal observation distance, the hood 51 is brought into abutting engagement with an intracavitary wall portion to stabilize a fore end portion of the insertion instrument 2. Upon projecting light from the illumination windows 11 within the hood 51 which is in abutted against an intracavitary wall, the illumination light is reflected on the surface of the subject S and then again on the inner surface of the hood 51. Consequently, the subject S under examination is also illuminated indirectly with reflected light which falls almost uniformly on the entire surfaces of the subject. In order to enhance the effects of indirect illumination by reflected light, the hood 51 is provided with a white reflecting surface on its inner periphery, which is preferably a rough irregular reflection surface which will contribute to suppress localized variations of indirect illumination.

With regard to an extension length of the hood 51 from the distal end of the endoscopic insertion instrument, it should be substantially equivalent with or longer than the minimal observation distance d. If the extension length of the hood 51 is shorter than the minimal observation distance d, the endoscopic observation means can be located at a distance smaller than the minimal observation distance d when the hood 51 is abutted against an intracavitary wall portion under examination. On the other hand, if the extension length of the hood 51 is conspicuously greater than the minimal observation distance d, it can obstruct the view field of the objective lens group 23 in the observation window 10.

EXAMPLES

Figure 11:
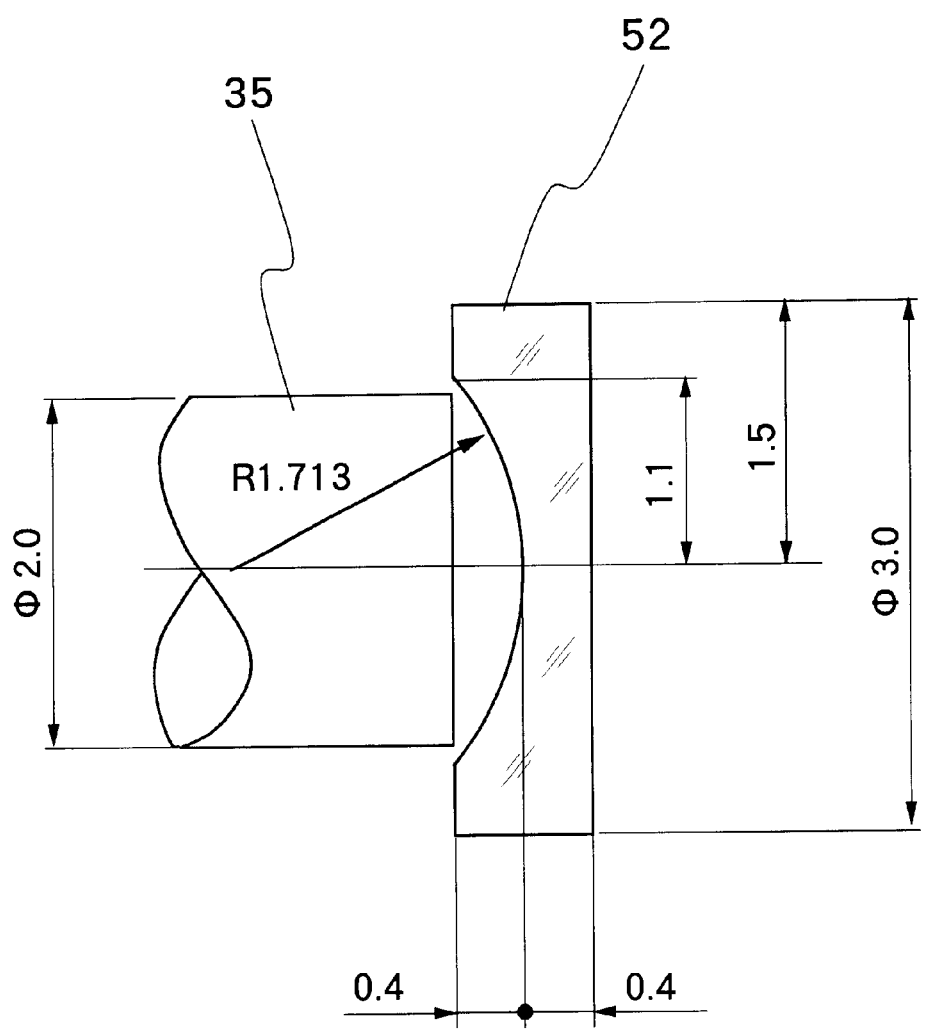
FIG. 11 is a diagrammatic illustration of light guide and illumination lens employed in first and second embodiments of the present invention.
Figure 12:
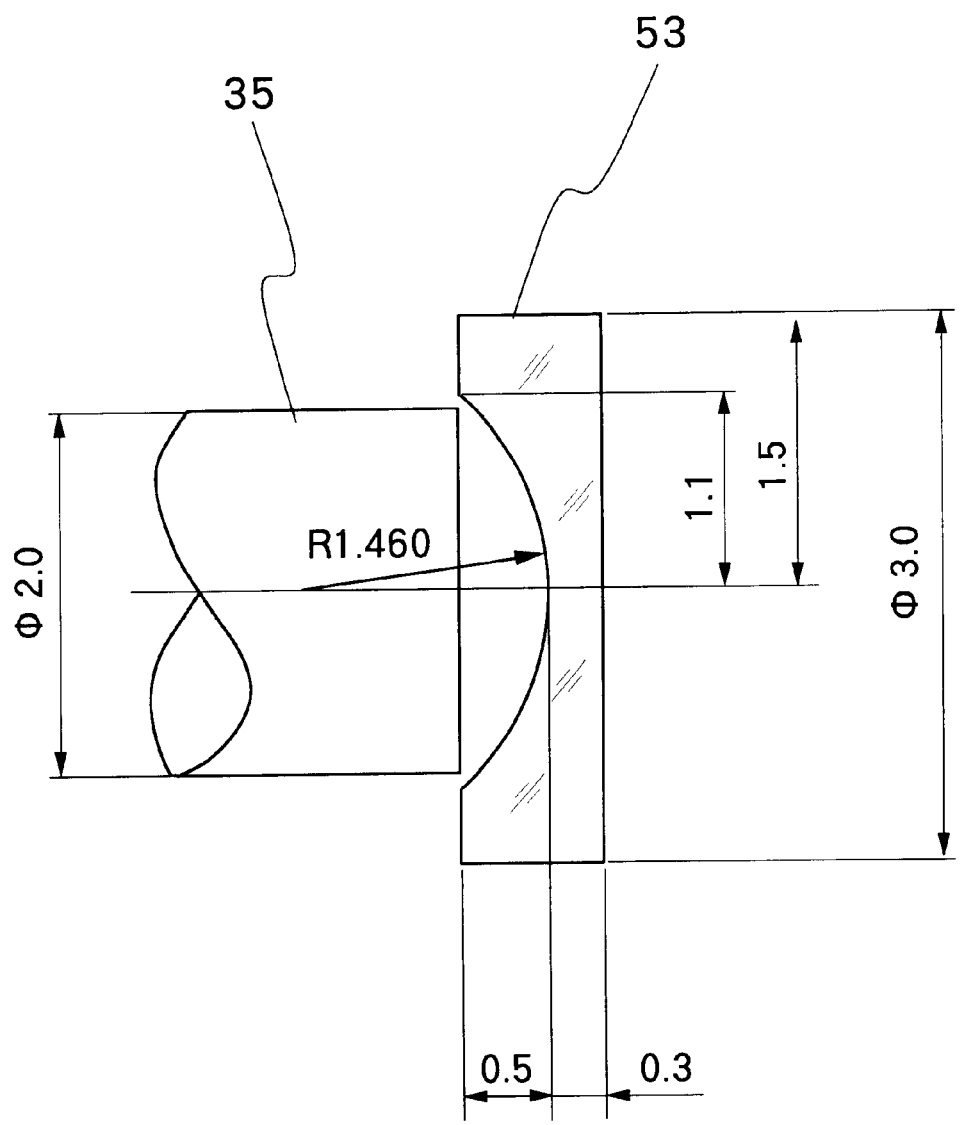
FIG. 12 is a diagrammatic illustration of light guide and illumination lens employed in third and fourth embodiments of the present invention.

Illustrated in FIG. 11 is a construction of an illumination lens 52 which is fitted in position within each illumination window in front of a light emitting end of a light guide 35. The illumination lens 52 is in the form of a plano-concave lens having a radius of curvature R=1.713 as shown in the drawing. This lens construction was employed for illumination lenses in Examples 1 and 2, which however had indices of refractivity of nd=1.55 and nd=1.85 for line d, respectively. Further, shown in FIG. 12 a construction of an illumination lens 53 similarly in the form of a plano-concave lens with a radius of curvature R=1.460. An illumination lens of this construction was fitted in position within each illumination window in front of a light emitting end of a light guide in Examples 3 and 4. The illumination lenses in Example 3 however had an index of refractivity nd=1.55, while the illumination lenses in Example 4 had an index of refractivity nd=1.85.

Figure 13:
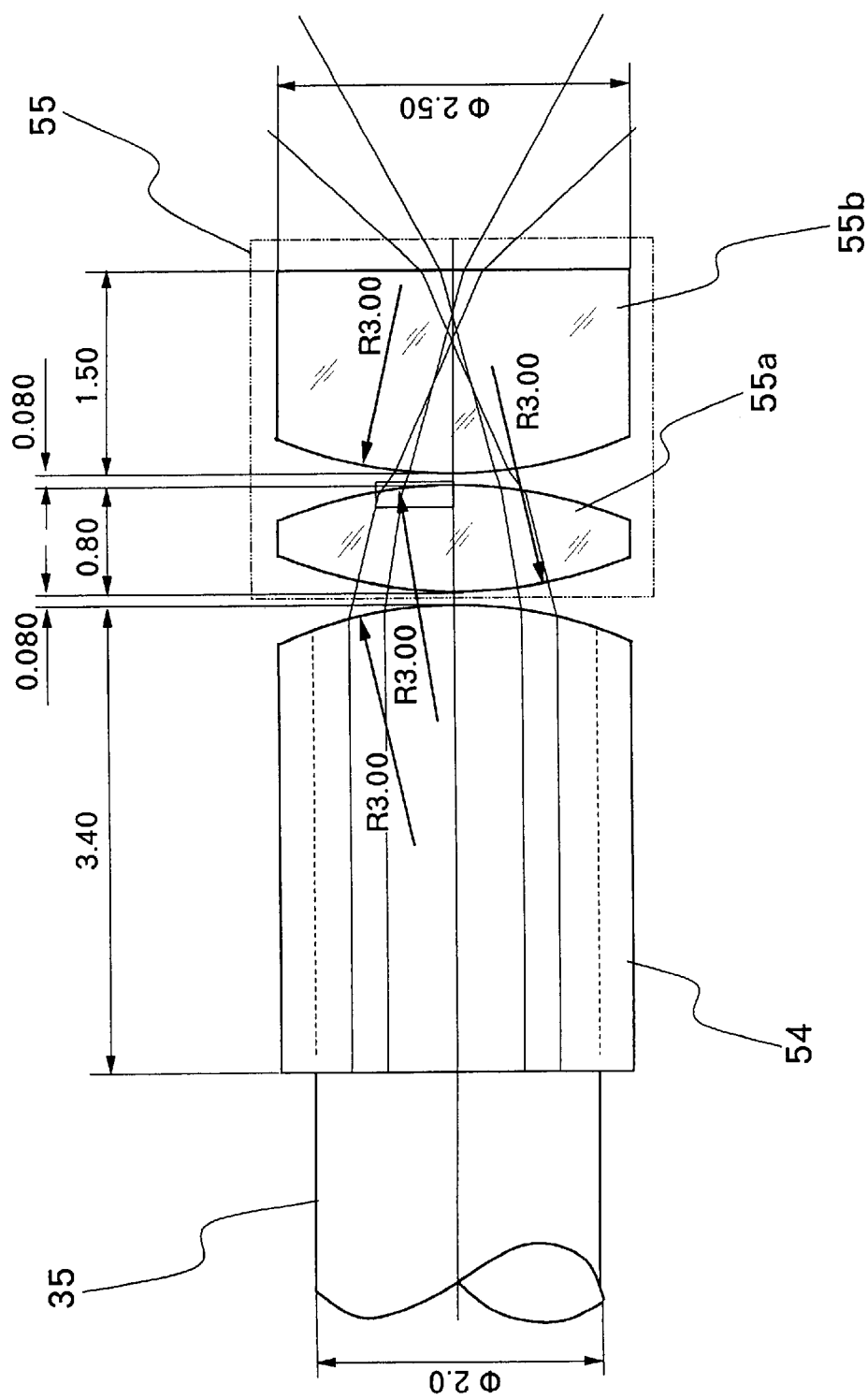
FIG. 13 is a diagrammatic illustration of light guide and illumination lens employed in fifth and sixth embodiments of the present invention.

Further shown in FIG. 13 is an example employing, at the light emitting end of a light guide 50, a light mixing and guiding glass rod 54 consisting of a core and a clad. The light mixing glass rod 54 is formed in a convex shape at its light emitting end disposed face to face with an illumination lens in the form of a composite lens element 55 consisting of a convex lens 55a and a plano-convex lens 55b. With an illumination lens system of this construction, illumination light is once converged toward a front side of the composite lens element 55 and then diverged toward a subject under observation. This illumination lens system was used in Examples 5 and 6. The light guide glass rod 54 was composed of a core of nd=1.62 and a clad of nd=1.52, and combined with a composite lens element 55 having nd=1.55 in Example 5 and nd=1.85 in Example 6. In this connection, shown in FIG. 13 are paths of light rays which are incident in parallel relation with the optical axis of the glass rod 54 having nd=1.85.

Table 1 below shows relative values in light emergence angle distribution in the respective Examples of illumination lenses.

In Table 1, figures indicated in the column "LG" are angular distribution of illuminating light emerging from the light emitting end of the light guide 35. Figures in the columns of Examples 1 to 6 are angular distributions of illuminating light coming out past the illumination lens systems of the respective Examples, indicated in angles with the optical axis of the irradiated illumination light and in percentages of a light volume at the most predominant angle.

TABLE 1

| Angle | LG | Ex. 1 | Ex. 2 | Ex. 3 | Ex. 4 | Ex. 5 | Ex. 6 |
|---|---|---|---|---|---|---|---|
| 0 | 100.0 | 100.0 | 100.0 | 100.0 | 100.0 | 98.1 | 100.0 |
| 5 | 98.3 | 97.8 | 98.4 | 99.5 | 98.6 | 100.0 | 99.7 |
| 10 | 94.0 | 91.8 | 94.3 | 95.4 | 95.8 | 95.0 | 98.6 |
| 15 | 87.9 | 83.5 | 88.6 | 89.4 | 91.9 | 92.8 | 96.7 |
| 20 | 78.9 | 72.9 | 81.0 | 80.3 | 86.5 | 85.1 | 94.4 |
| 25 | 65.0 | 61.5 | 71.4 | 70.3 | 78.9 | 76.2 | 90.9 |
| 30 | 47.7 | 49.5 | 60.9 | 59.3 | 69.7 | 63.8 | 87.4 |
| 35 | 32.5 | 38.8 | 50.2 | 48.5 | 60.8 | 51.2 | 82.9 |
| 40 | 16.7 | 28.9 | 40.5 | 37.9 | 51.4 | 38.7 | 77.3 |
| 45 | 5.2 | 20.3 | 31.7 | 28.5 | 43.0 | 28.9 | 69.6 |
| 50 | 1.0 | 13.5 | 24.1 | 20.4 | 34.9 | 20.5 | 60.0 |
| 55 | 0.1 | 8.5 | 17.9 | 13.9 | 27.1 | 13.8 | 49.2 |
| 60 | 0.0 | 4.9 | 12.8 | 8.9 | 20.5 | 7.2 | 37.7 |
| 65 | 0.0 | 2.6 | 8.9 | 5.3 | 15.1 | 2.6 | 26.3 |
| 70 | 0.0 | 1.2 | 5.9 | 3.0 | 10.8 | 0.3 | 16.1 |
| 75 | 0.0 | 0.5 | 3.5 | 1.4 | 6.9 | 0.0 | 8.5 |
| 80 | 0.0 | 0.2 | 1.7 | 0.6 | 3.2 | 0.0 | 3.4 |
| 85 | 0.0 | 0.1 | 0.7 | 0.2 | 1.4 | 0.0 | 1.2 |
| 90 | 0.0 | 0.0 | 0.0 | 0.0 | 0.0 | 0.0 | 0.0 |

Figure 14:
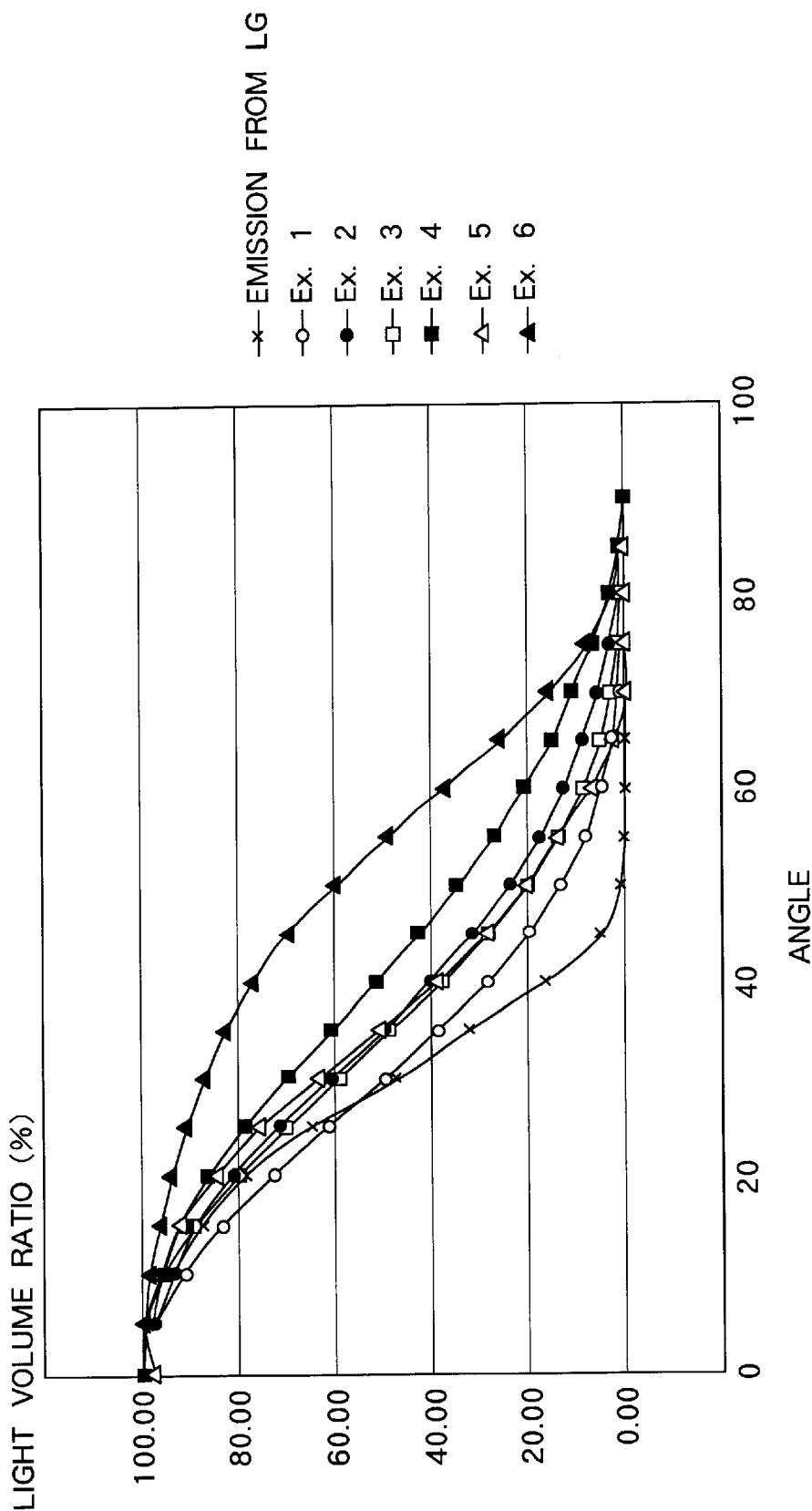
FIG. 14 is a diagram of light distributions by the illumination lenses employed in the first to sixth embodiments.
Figure 15:
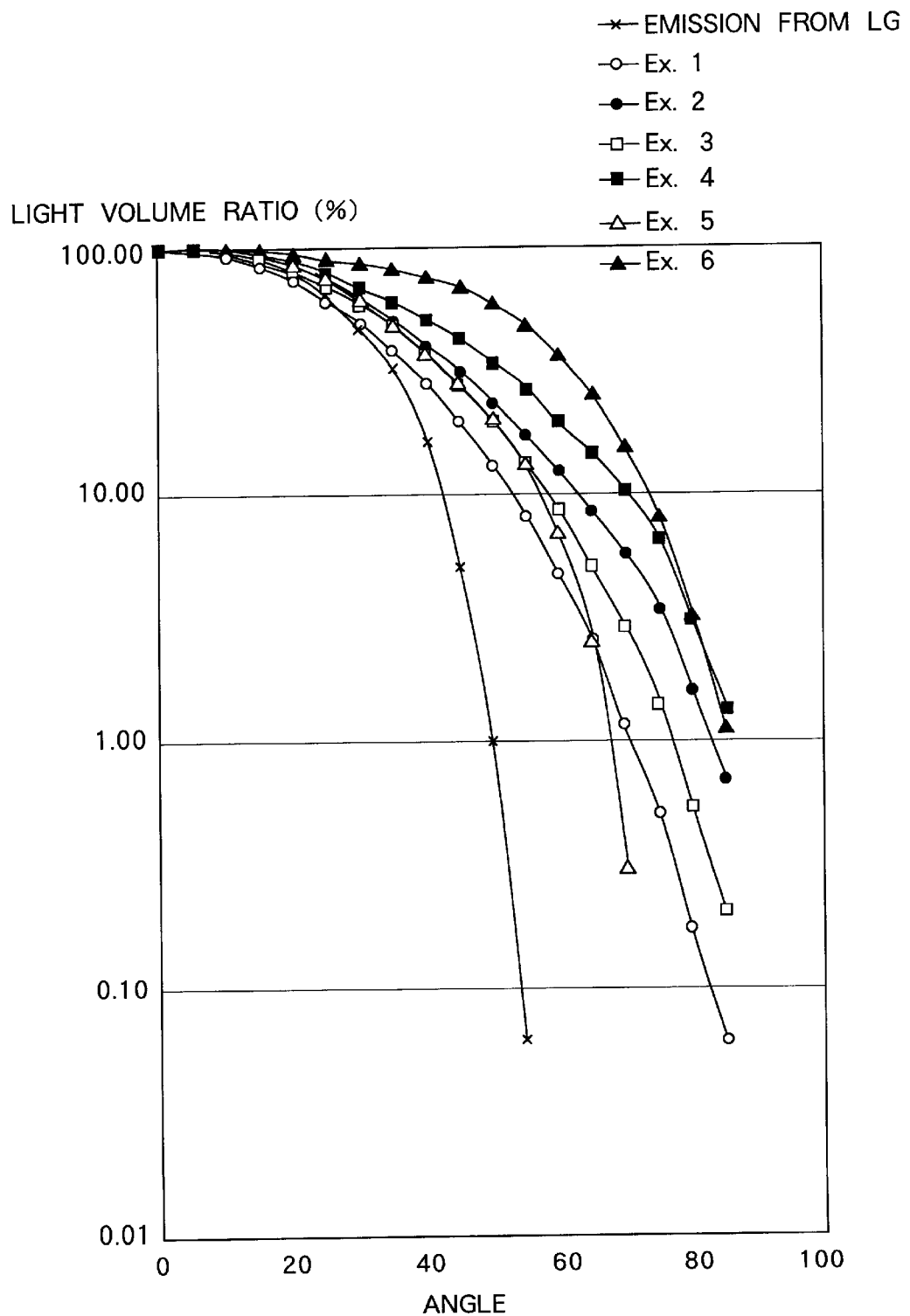
FIG. 15 is a logarithmic presentation of the light distributions shown in FIG. 14.

The figures in Table 1 above are plotted in the graph of FIG. 14. The same data are logarithmically presented in the graph of FIG. 15. Thus, on the basis of the light distribution characteristics of the singular or composite illumination lens elements given in Table 1 and in the graphs of FIGS. 14 and 15, the positions of the illumination windows 11 on the opposite sides of the observation window 10 can be determined in such a way as to distribute the illumination light as uniformly as possible from a minimal observation distance position. More particularly, the distance of each illumination means from the observation means is obtained from $S \cdot \sin \theta$, in which S is a length of a straight line which connects two points on a curve in FIG. 14 (two end points of a segment where light volume at a higher point is not greater than 200% of that at a lower point), and $\theta$ is a rising angle.

What is claimed is:

1. An endoscopic observation system, comprising:

an optical image pickup system having an objective lens of a variable observation distance to pick up images of a subject through an observation window provided at a distal end of an endoscopic insertion instrument;

an illumination system having at least a couple of illumination means located on the opposite sides of and substantially in the same plane as said observation window of said optical image pickup system;

said illumination means each having a light guide and an illumination lens for diverging illuminating light from said light guide toward a subject under examination;

said illumination means on the opposite sides of said observation window being located in positions spaced from said observation window by such a distance as to hold illuminance in peripheral portions of an imaging area of said subject to a level lower than 200% of an illuminance level in a center portion of said imaging area at the time of observation from a minimal observation distance of said objective lens.

2. An endoscopic observation system as defined in claim 1, wherein said illumination means are spaced apart by such a distance as to hold illuminance in peripheral portions of said imaging area of said subject in a range of 200% to 120% of an illuminance level in a center portion of said imaging area.

3. An endoscopic observation system as defined in claim 1, wherein said optical image pickup system further comprises a solid-state image sensor device for picking up images of a subject to be displayed on a monitor screen, and said peripheral portions of said image area are end portions of an image area on said monitor screen.

4. An endoscopic observation system as defined in claim 3, further comprising a gain controller for increasing gain of said solid-state image sensor device at the time of observation from said minimal observation distance.

5. An endoscopic observation system as defined in claim 1, wherein said minimal observation distance of said objective lens is shorter than 1 cm.

6. An endoscopic observation system as defined in claim 1, wherein said illumination system further comprises a volume control to increase illumination light to a greater volume at the time of an observation from said minimal observation distance than in observations from ordinary distances.

7. An endoscopic observation system as defined in claim 6 wherein said volume control is constituted by either a source volume adjusting means or a third illumination means located between said two illumination means.

8. An endoscopic observation system as defined in claim 6 further comprising a reversible motor for displacing a movable lens element or elements of said objective lens, said volume control being adapted to increase the volume of illumination light when said movable lens element is shifted to a minimal observation distance position by said reversible motor.

9. An endoscopic observation system as defined in claim 1, further comprising an annular hood member detachably fitted on said distal end of said insertion instrument, said hood member being provided with a reflecting surface on inner periphery thereof.

10. An endoscopic observation system as defined in claim 9, wherein said food member is extended forward of said distal end of said insertion instrument by a length substantially equivalent with said minimal observation distance or by a greater length as long as non-obstructive to an observation view field of said observation means.

* * * * *